United States Patent
Rama Swamy Chowdary et al.

(10) Patent No.: US 11,730,753 B2
(45) Date of Patent: Aug. 22, 2023

(54) STABLE PHARMACEUTICAL COMPOSITIONS COMPRISING TRIFLURIDINE AND TIPIRACIL HYDROCHLORIDE

(71) Applicant: NATCO PHARMA LIMITED, Hyderabad (IN)

(72) Inventors: Tripuraneni Rama Swamy Chowdary, Hyderabad (IN); Bhavanasi Krishna Murthy, Hyderabad (IN); Yedluri Siddhartha, Hyderabad (IN); Bhat Pavan, Hyderabad (IN); Nannapaneni Venkaiah Chowdary, Hyderabad (IN)

(73) Assignee: Natco Pharma Limited, Hyderabad (IN)

( * ) Notice: Subject to any disclaimer, the term of this patent is extended or adjusted under 35 U.S.C. 154(b) by 0 days.

(21) Appl. No.: 16/977,802

(22) PCT Filed: Mar. 2, 2019

(86) PCT No.: PCT/IN2019/050182
§ 371 (c)(1),
(2) Date: Sep. 2, 2020

(87) PCT Pub. No.: WO2019/171394
PCT Pub. Date: Sep. 12, 2019

(65) Prior Publication Data
US 2020/0405741 A1 Dec. 31, 2020

(30) Foreign Application Priority Data
Mar. 3, 2018 (IN) .............................. 201841007904

(51) Int. Cl.
*A61K 31/7072* (2006.01)
*A61K 9/20* (2006.01)
*A61K 31/513* (2006.01)

(52) U.S. Cl.
CPC ........ *A61K 31/7072* (2013.01); *A61K 9/2059* (2013.01); *A61K 9/2095* (2013.01); *A61K 31/513* (2013.01)

(58) Field of Classification Search
CPC .............. A61K 31/7072; A61K 9/2059; A61K 9/2095; A61K 31/513
See application file for complete search history.

(56) References Cited

U.S. PATENT DOCUMENTS

| 3,201,387 | A | 8/1965 | Heidelberger |
| 5,744,475 | A | 4/1998 | Yano et al. |
| 6,479,500 | B1 | 11/2002 | Fukushima et al. |
| 7,799,783 | B2 | 9/2010 | Emura et al. |
| 9,527,833 | B2 | 12/2016 | Kazuno et al. |
| 2014/0356431 | A1 | 12/2014 | Ohnishi |
| 2014/0363512 | A1* | 12/2014 | Ohnishi ............. A61K 31/7072 424/490 |
| 2017/0057949 | A1 | 3/2017 | Kazuno et al. |

FOREIGN PATENT DOCUMENTS

| CN | 106913580 A | 7/2017 |
| WO | 2018/167256 A1 | 9/2018 |

OTHER PUBLICATIONS

Google_search_1-13-22_lonsurf_excipients.pdf (Year: 2022).*
Google_scholar_search_1-13-22_lonsurf_excipients.pdf (Year: 2022).*
Google_patent_search_1-13-22__composition__trifluridine__pregelatinized_starch__tablet.pdf (Year: 2022).*

* cited by examiner

*Primary Examiner* — Michael P Cohen
(74) *Attorney, Agent, or Firm* — Melissa M. Hayworth; E. Joseph Gess

(57) ABSTRACT

The present invention relates to pharmaceutical compositions comprising trifluridine and tipiracil hydrochloride. More particularly, the present invention relates to a tablet composition comprising trifluridine, tipiracil hydrochloride and one or more pharmaceutically acceptable excipients and process for preparing such compositions.

5 Claims, No Drawings

STABLE PHARMACEUTICAL COMPOSITIONS COMPRISING TRIFLURIDINE AND TIPIRACIL HYDROCHLORIDE

FIELD OF THE INVENTION

The present invention relates to stable pharmaceutical compositions comprising trifluridine and tipiracil hydrochloride. More particularly, the present invention relates to a stable tablet composition comprising trifluridine, tipiracil hydrochloride and one or more pharmaceutically acceptable excipients and process for preparing such compositions.

BACKGROUND OF THE INVENTION

Trifluridine (FTD) is an antineoplastic thymidine-based nucleoside analogue and is described chemically as 2'-deoxy-5-(trifluoromethyl) uridine or α,α,α-trifluorothymidine. Trifluridine is first disclosed in U.S. Pat. No. 3,201,387.

Tipiracil hydrochloride (TPI) is a thymidine phosphorylase inhibitor and is described chemically as 5-chloro-6-[(2-iminopyrrolidin-1-yl)methyl]pyrimidine-2,4-(1H,3H)-dione mono hydrochloride or 2,4(1H,3H)-pyrimidinedione, 5-chloro-6-[(2-imino-1-pyrrolidinyl) methyl]-, hydrochloride (1:1) or 5-chloro-6-(1-(2-iminopyrrolidinyl)methyl)uracil hydrochloride. Tipiracil hydrochloride is first disclosed in U.S. Pat. No. 5,744,475.

The combination of trifluridine and tipiracil hydrochloride in a molar ratio of 1:0.5 approved as an anti-tumour agent (TAS-102) in the form of tablets and marketed under the brand name LONSURF® by Taiho Pharmaceuticals.

The combination product of trifluridine and tipiracil hydrochloride is indicated for the treatment of patients with metastatic colorectal cancer who have been previously treated with fluoropyrimidine, oxaliplatin and irinotecan-based chemotherapy, an anti-VEGF biological therapy, and if RAS wild-type, an anti-EGFR therapy.

LONSURF is also indicated for the treatment of adult patients with metastatic gastric or gastroesophageal junction adenocarcinoma previously treated with at least two prior lines of chemotherapy that included a fluoropyrimidine, a platinum, either a taxane or irinotecan, and if appropriate, HER2/neu-targeted therapy.

U.S. Pat. No. 6,479,500 discloses a method for alleviating side effects caused by use of an anti-tumor agent comprising administering tipiracil in a patient to whom an anti-tumor agent has been administered.

U.S. Pat. No. 7,799,783 discloses a method for treating cancer, comprising administering to patients in need of cancer therapy a composition containing trifluridine and tipiracil hydrochloride in a molar ratio of 1:0.5, at an oral dose of 20 to 80 mg/m²/day in terms of FTD in 2 to 4 divided portions.

U.S. Pat. No. 9,527,833 discloses crystal Form I of tipiracil hydrochloride.

US 2017/0057949 discloses crystal Form III of tipiracil hydrochloride.

US 2014/0356431 discloses a pharmaceutical composition comprising trifluridine and tipiracil hydrochloride as active ingredients and a sugar having a critical relative humidity of 85% or more at 25° C. as an excipient. This publication further discloses that sugars having a critical relative humidity of 85% or more at 25° C. preferably a disaccharide or a sugar alcohol when added as a excipient, suppresses the increase in related substances of trifluridine and tipiracil even after storage under high-humidity conditions. The content of the sugar having a critical relative humidity of 85% or more in the orally administrable pharmaceutical composition of the present invention is, from viewpoints of the stability of trifluridine and TPI and of the function as an excipient, preferably 3.6 parts by mass or more, more preferably from 3.6 to 50 parts by mass, still more preferably from 3.7 to 25 parts by mass, and particularly preferably from 3.7 to 10 parts by mass, based on 1 part by mass of trifluridine. It also discloses that the composition comprises a disintegrating agent preferably partly pregelatinized starch in an amount of 2-16% w/w of the composition.

US 2014/0363512 discloses an oral pharmaceutical composition comprising trifluridine and tipiracil hydrochloride as an active ingredient; and being substantially free of an additive comprising a metal salt. It has been proved that the amount of FTD and TPI related substances were increased when stored particularly under high-humidity conditions depending on types of formulation additives added. This publication further discloses that metal salts increases the formation of related substances of trifluridine and tipiracil and the metal salts include alkali metal salts and alkaline earth metal salts. Further, it discloses that, from a viewpoint of the stability of the active ingredients, it is preferred to be particularly free of alkaline earth metal salts, and furthermore, it is more preferred to be free of talc, carmellose calcium, and magnesium stearate.

The above prior art references discloses different compositions to improve the stability of trifluridine and tipiracil hydrochloride. Still, there exists a need to develop an alternative stable pharmaceutical composition comprising trifluridine and tipiracil hydrochloride. US 2014/0356431 discloses that sugars having a critical relative humidity of 85% or more at 25° C. preferably a disaccharide or a sugar alcohol when added as a excipient in an amount of 3.6 parts by mass or more based on 1 part by mass of trifluridine, suppresses the increase in related substances of trifluridine and tipiracil. US 2014/0363512 discloses that the presence of metal salt increases the formation of related substances of trifluridine and tipiracil. However, the inventors of the present invention have surprisingly found that a tablet composition comprising trifluridine, tipiracil hydrochloride, 16-25% w/w of pregelatinized starch even in the presence of metal salt and a sugar having a critical relative humidity of 85% or more at 25° C. in an amount of less than 3.6 parts by mass based on 1 part by mass of trifluridine was found to be stable even after storing at high temperature and relative humidity conditions.

OBJECTIVE OF THE INVENTION

The main objective of the present invention relates to a stable pharmaceutical composition comprising trifluridine, tipiracil hydrochloride and one or more pharmaceutically acceptable excipients.

The present invention also relates to a stable tablet composition comprising trifluridine, tipiracil hydrochloride and one or more pharmaceutically acceptable excipients.

The present invention also relates to a process for the preparation of a stable tablet composition comprising trifluridine, tipiracil hydrochloride and one or more pharmaceutically acceptable excipients having comparable dissolution properties, content uniformity and equivalent bioavailability w.r.t marketed trifluridine+tipiracil hydrochloride dosage form.

SUMMARY OF THE INVENTION

Accordingly, the present invention provides a stable composition comprising trifluridine, tipiracil hydrochloride and one or more pharmaceutically acceptable excipients.

The present invention also relates to a stable tablet composition comprising trifluridine, tipiracil hydrochloride, more than 16% w/w of a disintegrating agent and one or more pharmaceutically acceptable excipients.

The present invention also relates to a stable tablet composition comprising trifluridine, tipiracil hydrochloride, more than 16% w/w of a disintegrating agent and one or more pharmaceutically acceptable excipients, wherein the composition contains an excipient which is a metal salt.

The present invention also relates to a stable tablet composition comprising trifluridine, tipiracil hydrochloride, more than 16% w/w of a disintegrating agent and one or more pharmaceutically acceptable excipients, wherein the composition is free of a sugar.

The present invention also relates to a stable tablet composition comprising trifluridine, tipiracil hydrochloride, 16-25% w/w of pregelatinized starch and one or more pharmaceutically acceptable excipients.

The present invention also relates to a stable tablet composition comprising trifluridine, tipiracil hydrochloride, 16-25% w/w of pregelatinized starch and one or more pharmaceutically acceptable excipients, wherein the composition contains a pharmaceutically acceptable excipient which is a metal salt.

The present invention also relates to a stable tablet composition comprising trifluridine, tipiracil hydrochloride, 16-25% w/w of pregelatinized starch and one or more pharmaceutically acceptable excipients, wherein the composition contains a pharmaceutically acceptable excipient which is a metal salt and wherein the composition comprises a sugar in an amount less than 3.6 parts by mass based on 1 part by mass of Trifluridine.

DETAILED DESCRIPTION OF THE INVENTION

The present invention also relates to a stable pharmaceutical composition comprising trifluridine, tipiracil hydrochloride and one or more pharmaceutically acceptable excipients.

The present invention also relates to a stable tablet composition comprising trifluridine, tipiracil hydrochloride and one or more pharmaceutically acceptable excipients.

The present invention also relates a process for the preparation of stable composition comprising trifluridine, tipiracil hydrochloride and one or more pharmaceutically acceptable excipients.

The present invention also relates a process for the preparation of stable tablet composition comprising trifluridine, tipiracil hydrochloride and one or more pharmaceutically acceptable excipients.

In another embodiment, "trifluridine" according to the present invention includes but not limited to trifluridine and its pharmaceutically acceptable salts, ethers, esters, prodrugs, polymorphs and derivatives thereof.

In another embodiment, "tipiracil" according to the present invention includes but not limited to tipiracil and its pharmaceutically acceptable salts, ethers, esters, prodrugs, polymorphs and derivatives thereof.

As used herein, the term "% w/w" refers to the weight of the component based on the total weight of a composition comprising the component.

"Pharmaceutically acceptable excipient/s" are the components added to pharmaceutical formulation to facilitate manufacture, enhance stability, control release, enhance product characteristics, enhance bioavailability, enhance patient acceptability, etc.

In another embodiment, the composition according to the present invention further comprises one or more pharmaceutically acceptable excipients which include but not limited to diluents/fillers, disintegrants/disintegrating agents, binders, surfactants, glidants and lubricants. These excipients may be present intragranularly or extragranularly.

Diluents/fillers according to the present invention include but not limited to lactose monohydrate, lactose anhydrous, fructose, dextrose, dextrates, dextrins, mannitol, lactitol, sorbitol, starch, sucrose, calcium carbonate, dibasic calcium phosphate, tribasic calcium phosphate, calcium sulfate, sodium chloride, microcrystalline cellulose, silicified microcrystalline cellulose, cellulose powdered, kaolin and the like or combinations thereof. The diluent/filler may be used in the range of 5-95% w/w of the composition.

Binders according to the present invention include but not limited to hydroxypropyl methylcellulose, hydroxypropyl cellulose, Polyvinylpyrrolidone (povidone), gelatin, ethyl cellulose, polyvinyl alcohol, pregelatinized starch, partially pregelatinized starch, carboxymethyl cellulose, sodium alginate, microcrystalline cellulose and the like or combinations thereof. The binder may be used in the range of 1-40% w/w of the composition.

Disintegrants/Disintegrating agents according to the present invention include but not limited to starches or modified starches such as pregelatinized starch, partly pregelatinized starch, partially pregelatinized starch; croscarmellose sodium, crospovidone, sodium starch glycolate, low substituted hydroxypropyl cellulose, hydroxypropyl cellulose, carmellose, carmellose calcium, carmellose sodium and the like or combinations thereof. The disintegrant may be used in the range of 1-30% w/w of the composition.

Surfactants according to the present invention may be selected from anionic, cationic or non-ionic surface-active agents or surfactants. Suitable anionic surfactants include but not limited to carboxylate, sulfonate, and sulfate ions such as sodium lauryl sulfate (SLS), sodium laurate, dialkyl sodium sulfosuccinates particularly bis-(2-ethylhexyl) sodium sulfosuccinate, sodium stearate, potassium stearate, sodium oleate and the like. Suitable cationic surfactants include but not limited to those containing long chain cations, such as benzalkonium chloride, bis-2-hydroxyethyl oleyl amine or the like. Suitable non-ionic surfactants include but not limited to polyoxyethylene sorbitan fatty acid esters (polysorbates), fatty alcohols such as lauryl, cetyl and stearyl alcohols; glyceryl esters such as the naturally occurring mono-, di-, and tri-glycerides; fatty acid esters of fatty alcohols; polyglycolized glycerides such as gelucire; polyoxyethylene-polyoxypropylene block co-polymer such as Poloxamer and other alcohols such as propylene glycol, polyethylene glycol. The surfactant may be used in the range of 0.001-5% w/w of the composition.

Lubricants/glidants according to the present invention include but not limited to colloidal silicon dioxide, stearic acid, magnesium stearate, calcium stearate, sodium stearyl fumarate, talc, hydrogenated castor oil, and mixtures thereof. The lubricant/glidant may be used in the range of 0.01-5% w/w of the composition.

In one embodiment, the present invention relates to a process for the preparation of a stable pharmaceutical composition, comprising the steps of:

(i) blending trifluridine, tipiracil hydrochloride with one or more pharmaceutically acceptable excipients,
(ii) formulating the blend of step (i) into suitable dosage form.

In another embodiment, the present invention relates to a process for the preparation of tablet composition, comprising the steps of:
(i) blending trifluridine, tipiracil hydrochloride with one or more pharmaceutically acceptable excipients,
(ii) compressing the blend of step (i) into tablet dosage form.

In another embodiment, the present invention relates to a process for the preparation of tablet composition, comprising the steps of:
(i) blending trifluridine, tipiracil hydrochloride with one or more pharmaceutically acceptable excipients,
(ii) lubricating the blend of step (i) with one or more lubricants, and
(iii) compressing the lubricated blend of step (ii) into tablet dosage form.

In another embodiment, the present invention relates to a process for the preparation of tablet composition, comprising the steps of:
(i) blending trifluridine, tipiracil hydrochloride with one or more pharmaceutically acceptable excipients,
(ii) lubricating the blend of step (i) with one or more lubricants,
(iii) compressing the lubricated blend of step (ii) into tablet dosage form, and
(iv) coating the tablets prepared in step (iii) with a coating composition.

In another embodiment, the present invention relates to a process for the preparation of tablet composition, comprising the steps of:
(i) blending trifluridine, tipiracil hydrochloride with one or more pharmaceutically acceptable excipients,
(ii) granulating the blend of step (i),
(iii) blending the granules of step (ii) with one or more pharmaceutically acceptable excipients, and
(iv) compressing the blend of step (iii) into tablet dosage form.

In another embodiment, the present invention relates to a process for the preparation of tablet composition, comprising the steps of:
(i) blending trifluridine, tipiracil hydrochloride with one or more pharmaceutically acceptable excipients,
(ii) granulating the blend of step (i),
(iii) blending the granules of step (ii) with one or more pharmaceutically acceptable excipients,
(iv) compressing the blend of step (iii) into tablet dosage form, and
(v) coating the tablets prepared in step (iv) with a coating composition.

In another embodiment, the present invention relates to a process for the preparation of tablet composition, comprising the steps of:
(i) blending trifluridine, tipiracil hydrochloride with one or more pharmaceutically acceptable excipients,
(ii) granulating the blend of step (i),
(iii) blending the granules of step (ii) with one or more pharmaceutically acceptable excipients,
(iv) lubricating the blend of step (iii) with one or more lubricants and
(iv) compressing the lubricated blend of step (iv) into tablet dosage form.

In another embodiment, the present invention relates to a process for the preparation of tablet composition, comprising the steps of:
(i) blending trifluridine, tipiracil hydrochloride with one or more pharmaceutically acceptable excipients,
(ii) granulating the blend of step (i),
(iii) blending the granules of step (ii) with one or more pharmaceutically acceptable excipients,
(iv) lubricating the blend of step (iii) with one or more lubricants,
(iv) compressing the lubricated blend of step (iv) into tablet dosage form and
(v) coating the tablets prepared in step (iv) with a coating composition.

In another embodiment, the present invention relates to a process for the preparation of tablet composition, comprising the steps of:
(i) blending trifluridine, tipiracil hydrochloride with one or more pharmaceutically acceptable excipients,
(ii) slugging the blend of step (i) and milling,
(iii) blending the milled granules of step (ii) with one or more pharmaceutically acceptable excipients,
(iv) lubricating the blend of step (iii) with one or more lubricants and
(iv) compressing the lubricated blend of step (iv) into tablet dosage form.

In another embodiment, the present invention relates to a process for the preparation of tablet composition, comprising the steps of:
(i) blending trifluridine, tipiracil hydrochloride with one or more pharmaceutically acceptable excipients,
(ii) slugging the blend of step (i) and milling,
(iii) blending the milled granules of step (ii) with one or more pharmaceutically acceptable excipients,
(iv) lubricating the blend of step (iii) with one or more lubricants,
(iv) compressing the lubricated blend of step (iv) into tablet dosage form and
(v) coating the tablets prepared in step (iv) with a coating composition.

In another embodiment, the pharmaceutical composition according to the present invention is in the form of tablets, capsules, granules, powder, pellets and sachets.

In another embodiment, the blend is formulated into a suitable dosage form like tablets or capsules using different techniques which are well known in the prior art.

In another embodiment, the compositions of the present invention may be prepared using any method known in the art, but are not limited to wet granulation, dry granulation, roller compaction, direct compression, melt granulation, solid dispersion, extrusion spherinization and encapsulation.

In another embodiment, the solvents used for granulation process may be selected from water, isopropyl alcohol, methanol, ethanol, methylene chloride or combination thereof.

The composition according to the present invention may be uncoated or optionally coated with functional coating, film coating, moisture barrier coating or a protective coating composition. The coating may be selected from amongst one or more of those suitable coating materials known in the art. Coating may be performed by applying one or more film forming polymers, with or without other pharmaceutically inert excipients, as a solution/suspension using any conventional coating technique known in the art, such as spray coating in a conventional coating pan or fluidized bed processor or dip coating.

The amount of the film coating may be about 1 to about 10% w/w, preferably, about 1 to about 3% w/w, of the total composition. Any of a variety of film coatings can be used in the present composition. Suitable film coating may include but not limited to polymers, plasticizers, pigments, opacifiers, glidants, binders, antitacking agents, antifoaming agents, surfactants, fillers, extenders, coloring agents and the like.

Examples of film-forming polymers include ethylcellulose, hydroxypropyl methylcellulose, polyvinyl alcohol (PVA), hydroxypropylcellulose, methylcellulose, carboxymethyl cellulose, hydroxymethylcellulose, hydroxyethylcellulose, cellulose acetate, hydroxypropyl methylcellulose phthalate, cellulose acetate phthalate, cellulose acetate trimellitate; waxes such as polyethylene glycol; methacrylic acid polymers such as Eudragit® RL and RS; and the like. Alternatively, commercially available coating compositions comprising film forming polymers marketed under various trade names, such as Opadry® may also be used for coating the tablets. The coating can be obtained as a dry blend concentrate.

The film coating may also optionally include a plasticizer such as triacetin, propylene glycol, diethyl phthalate, tributyl sebacate or polyethylene glycol (PEG), preferably PEG; and an anti-adherent or glidant such as talc, fumed silica or magnesium stearate, an opacifying agent such as titanium dioxide.

Coloring agent may be selected from FDA approved colorants such as Iron Oxide, Lake of Tartrazine, Allura Red, Lake of Quinoline Yellow, Lake of Erythrosine, titanium dioxide and the like.

The coating according to the present invention is applied by solubilising or suspending the excipients in solvents such as isopropyl alcohol, water, acetone, ethanol, methylene chloride, hydrochloric acid and the like, or mixtures thereof.

In one embodiment, the present invention provides a composition comprising trifluridine, tipiracil hydrochloride, disintegrating agent in an amount of 16-25% w/w of the composition and one or more pharmaceutically acceptable excipients.

In another embodiment, the present invention provides a composition comprising trifluridine, tipiracil hydrochloride, disintegrating agent in an amount of 16-25% w/w of the composition and one or more pharmaceutically acceptable excipients, wherein the composition contains a pharmaceutically acceptable excipient which is a metal salt.

In another embodiment, the present invention provides a composition comprising trifluridine, tipiracil hydrochloride, disintegrating agent in an amount of 16-25% w/w of the composition and one or more pharmaceutically acceptable excipients, wherein the composition is free of a sugar.

In another embodiment, the present invention provides a composition comprising trifluridine, tipiracil hydrochloride, disintegrating agent in an amount of 16-25% w/w of the composition and one or more pharmaceutically acceptable excipients, wherein the composition comprises a sugar in an amount less than 3.6 parts by mass based on 1 part by mass of trifluridine.

In another embodiment, the present invention provides a composition comprising trifluridine, tipiracil hydrochloride, disintegrating agent in an amount of 16-25% w/w of the composition and one or more pharmaceutically acceptable excipients, wherein the composition contains a pharmaceutically acceptable excipient which is a metal salt and wherein the composition is free of a sugar.

In another embodiment of the present invention, the pharmaceutically acceptable excipient which is a metal salt is selected from magnesium stearate, calcium stearate, sodium stearyl fumarate, carmellose calcium, carmellose sodium, sodium starch glycolate and combination thereof.

In another embodiment of the present invention, the content of the metal salts is preferably from 0.01 to 0.2 parts by mass, more preferably from 0.05 to 0.15 parts by mass, still more preferably from 0.1 to 0.13 parts by mass, based on 1 part by mass of trifluridine.

In another embodiment, the present invention provides a stable tablet composition comprising trifluridine, tipiracil hydrochloride, 16-25% w/w of pregelatinized starch and one or more pharmaceutically acceptable excipients.

In another embodiment, the present invention provides a stable tablet composition comprising trifluridine, tipiracil hydrochloride, 16-25% w/w of pregelatinized starch and one or more pharmaceutically acceptable excipients, wherein the composition contains a pharmaceutically acceptable excipient which is a metal salt.

In another embodiment, the present invention provides a stable tablet composition comprising trifluridine, tipiracil hydrochloride, 16-25% w/w of pregelatinized starch and one or more pharmaceutically acceptable excipients, wherein the composition contains a pharmaceutically acceptable excipient which is a metal salt and wherein the composition is free of a sugar.

In another embodiment, the present invention provides a stable tablet composition comprising trifluridine, tipiracil hydrochloride, 16-25% w/w of pregelatinized starch and one or more pharmaceutically acceptable excipients, wherein the composition contains a pharmaceutically acceptable excipient which is a metal salt and wherein the composition comprises a sugar in an amount less than 3.6 parts by mass based on 1 part by mass of trifluridine.

In another embodiment of the present invention, the composition is free of a sugar which have a critical relative humidity of 85% or more at 25° C. and the sugar is a disaccharide or sugar alcohols which is selected from one or more of lactose (including anhydride and hydrate), sucrose, mannitol, trehalose, maltose, maltitol, erythritol and combinations thereof.

The content of the sugar having a critical relative humidity of 85% or more in the composition of the present invention is, preferably less than 3.6 parts by mass, more preferably less than 3.0 based on 1 part by mass of trifluridine.

In another embodiment of the present invention, the composition comprises trifluridine in an amount of 1-40% w/w of the composition.

In another embodiment of the present invention, the composition comprises tipiracil in an amount of 1-40% w/w of the composition.

In another embodiment, the pharmaceutical composition according to the present invention is in the form of tablets, preferably immediate release tablets.

In another embodiment, the pharmaceutical composition according to the present invention is in the form of tablets which may be coated or uncoated.

In another embodiment, the tablet according to the present invention may be round or oval. The edges of the tablets can be beveled or rounded. In another embodiment, the tablets are ovoid or round. The tablets according to the invention may be scored.

In another embodiment, the present invention provides a composition comprising trifluridine in the range of about 1 mg to about 100 mg.

In another embodiment, the present invention provides a composition comprising tipiracil hydrochloride in the range of about 0.1 mg to about 50 mg.

In another embodiment, the composition comprising trifluridine and tipiracil according to the present invention can be used for the treatment of cancer by administering to patients in need of cancer therapy.

In another embodiment, the composition comprising trifluridine and tipiracil according to the present invention can be used for the treatment of patients with metastatic colorectal cancer who have been previously treated with fluoropyrimidine, oxaliplatin and irinotecan-based chemotherapy, an anti-VEGF biological therapy, and if RAS wild-type, an anti-EGFR therapy.

The invention is further illustrated by the following examples which are provided to be exemplary of the invention and do not limit the scope of the invention. While the present invention has been described in terms of its specific embodiments, certain modifications and equivalents will be apparent to those skilled in the art and are intended to be included within the scope of the present invention.

Example-1: Tablet Composition Comprising Trifluridine and Tipiracil Hydrochloride

| S. No | Ingredients | Quantity per tablet mg/tablet | % w/w |
|---|---|---|---|
| 1 | Trifluridine | 20.00 | 16.66 |
| 2 | Tipiracil hydrochloride | 9.42 | 7.85 |
| 3 | Microcrystalline cellulose | 64.73 | 53.94 |
| 4 | Partially Pregelatinised Starch | 24.00 | 20.00 |
| 5 | Stearic acid | 1.60 | 1.33 |
| 6 | Magnesium stearate | 0.25 | 0.20 |
|   | Core Tablet weight | 120.00 | 100.00 |
|   | Film Coating |   |   |
| 7 | Opadry ® | 2.60 | — |
|   | Coated Tablet Weight | 122.60 | — |

The processing steps involved in manufacturing the tablets comprising trifluridine and tipiracil hydrochloride were given below:

(i) Trifluridine, tipiracil hydrochloride, microcrystalline cellulose and partially pregelatinized starch were sifted separately and blended, (ii) the blend of step (i) was lubricated with stearic acid followed by magnesium stearate, (iii) the lubricated blend of step (ii) was compressed into tablets, and (iv) the tablets prepared in step (iii) were coated with Opadry® film coating composition.

Example-2

| S. No | Ingredients | Quantity per tablet mg/tablet | % w/w |
|---|---|---|---|
| 1 | Trifluridine | 20.00 | 16.66 |
| 2 | Tipiracil hydrochloride | 9.42 | 7.85 |
| 3 | Lactose | 64.73 | 53.94 |
| 4 | Partially Pregelatinised Starch | 24.00 | 20.00 |
| 5 | Stearic acid | 1.60 | 1.33 |
| 6 | Magnesium stearate | 0.25 | 0.20 |
|   | Core Tablet weight | 120.00 | 100.00 |
|   | Film Coating |   |   |
| 7 | Opadry ® | 2.60 | — |
|   | Coated Tablet Weight | 122.60 | — |

Example-3

| S. No | Ingredients | Quantity per tablet mg/tablet | % w/w |
|---|---|---|---|
| 1 | Trifluridine | 20.00 | 16.66 |
| 2 | Tipiracil hydrochloride | 9.42 | 7.85 |
| 3 | Microcrystalline cellulose | 64.98 | 54.15 |
| 4 | Crospovidone | 22.00 | 18.33 |
| 5 | Croscarmellose sodium | 2.00 | 1.66 |
| 6 | Stearic acid | 1.60 | 1.33 |
|   | Core Tablet weight | 120.00 | 100.00 |
|   | Film Coating |   |   |
| 7 | Opadry ® | 2.60 | — |
|   | Coated Tablet Weight | 122.60 | — |

Example-4

| S. No | Ingredients | Quantity per tablet mg/tablet | % w/w |
|---|---|---|---|
| 1 | Trifluridine | 20.00 | 16.66 |
| 2 | Tipiracil hydrochloride | 9.42 | 7.85 |
| 3 | Microcrystalline cellulose | 66.73 | 55.60 |
| 4 | Low substituted hydroxypropyl cellulose | 22.00 | 18.33 |
| 5 | Stearic acid | 1.60 | 1.33 |
| 6 | Magnesium stearate | 0.25 | 0.20 |
|   | Core Tablet weight | 120.00 | 100.00 |
|   | Film Coating |   |   |
| 7 | Opadry ® | 2.60 | — |
|   | Coated Tablet Weight | 122.60 | — |

The compositions given in Examples 2-4 were prepared using similar procedure described in Example-1.

Example-5

| S. No | Ingredients | Quantity per tablet mg/tablet | % w/w |
|---|---|---|---|
|   | Intragranular |   |   |
| 1 | Trifluridine | 20.00 | 17.09 |
| 2 | Tipiracil hydrochloride | 9.42 | 8.05 |
| 3 | Lactose monohydrate | 44.28 | 37.84 |
| 4 | Pregelatinized starch | 23.00 | 19.65 |
| 5 | Stearic acid | 3.00 | 2.56 |
|   | Extragranular |   |   |
| 6 | Lactose monohydrate | 15.00 | 12.82 |
| 7 | Magnesium stearate | 2.30 | 1.96 |
|   | Core Tablet weight | 117.00 | 100.00 |
|   | Film Coating |   |   |
| 8 | Opadry ® | 3.0 | — |
|   | Coated Tablet Weight | 120.00 | — |

The processing steps involved in manufacturing the tablets comprising trifluridine and tipiracil hydrochloride were given below:

(i) Trifluridine, tipiracil hydrochloride, lactose monohydrate, Pregelatinized starch and stearic acid were sifted separately and blended,
(ii) the blend of step (i) was slugged and milled,
(iii) the milled granules of step (ii) were blended with lactose monohydrate and lubricated with magnesium stearate,
(iv) the lubricated blend of step (iii) was compressed into tablets, and
(iv) the tablets prepared in step (iv) were coated with Opadry® film coating composition.

Stability Data: Table 2 given below shows the impurity profile of Trifluridine+Tipiracil hydrochloride tablets prepared according to Example 2 after storing at 40° C./75% RH for 6 months.

TABLE 2

Stability data of Trifluridine + Tipiracil hydrochloride tablets prepared according to Example 2 after storing in Blister pack at 40° C./75% RH for 6 months

| Impurities | Initial (% w/w) | 6 months (% w/w) |
|---|---|---|
| For Trifluridine | | |
| Related Compound A | 0.005 | 0.003 |
| Uracil | 0.009 | 0.050 |
| Unknown Impurity 1 | 0.071 | 0.003 |
| Unknown Impurity 2 | 0.009 | 0.008 |
| Unknown Impurity 3 | 0.022 | 0.035 |
| Unknown Impurity 4 | 0.003 | 0.004 |
| For Tipiracil hydrochloride | | |
| Impurity TPG | 0.091 | 0.152 |
| Impurity C | 0.023 | 0.047 |
| Unknown Impurity 1 | 0.006 | 0.071 |
| Unknown Impurity 2 | 0.013 | 0.000 |
| Unknown Impurity 3 | 0.184 | 0.022 |

We claim:

1. A stable tablet composition comprising trifluridine, tipiracil hydrochloride, 19-20% w/w of pregelatinized starch, lactose or lactose monohydrate, magnesium stearate, and optionally one or more additional pharmaceutically acceptable excipients, wherein the composition contains the magnesium stearate in an amount of 0.115 parts by mass based on 1 part by mass of trifluridine and the lactose or lactose monohydrate in an amount of 2.96 parts by mass based on 1 part by mass trifluridine.

2. The stable tablet composition of claim 1, comprising 17.09% w/w trifluridine and 8.05% w/w tipiracil hydrochloride.

3. A stable tablet composition comprising trifluridine, tipiracil hydrochloride, 19.65% w/w of pregelatinized starch, 1.96% w/w magnesium stearate, 50.66% w/w lactose monohydrate, wherein the composition contains the magnesium stearate in an amount of 0.115 parts by mass based on 1 part by mass of trifluridine and the lactose monohydrate in an amount of 2.96 parts by mass based on 1 part by mass trifluridine.

4. The stable tablet composition of claim 3, comprising 17.09% w/w trifluridine and 8.05% w/w tipiracil hydrochloride.

5. A stable tablet composition consisting of:

| S. No | Ingredients | Quantity per tablet | |
|---|---|---|---|
| | | mg/tablet | % w/w |
| | Intragranular | | |
| 1 | Trifluridine | 20.00 | 17.09 |
| 2 | Tipiracil hydrochloride | 9.42 | 8.05 |
| 3 | Lactose monohydrate | 44.28 | 37.84 |
| 4 | Pregelatinized starch | 23.00 | 19.65 |
| 5 | Stearic acid | 3.00 | 2.56 |
| | Extragranular | | |
| 6 | Lactose monohydrate | 15.00 | 12.82 |
| 7 | Magnesium stearate | 2.30 | 1.96 |
| | Core Tablet weight | 117.00 | 100.00 |
| | Film Coating | | |
| 8 | Opadry ® | 3.0 | — |
| | Coated Tablet Weight | 120.00 | —. |

* * * * *